United States Patent
Jackson

(10) Patent No.: US 9,844,305 B1
(45) Date of Patent: Dec. 19, 2017

(54) KIT OF TOILETRY ITEMS

(71) Applicant: Hobokela Jackson, Bon Air, AL (US)

(72) Inventor: Hobokela Jackson, Bon Air, AL (US)

( * ) Notice: Subject to any disclaimer, the term of this patent is extended or adjusted under 35 U.S.C. 154(b) by 0 days.

(21) Appl. No.: 15/363,003

(22) Filed: Nov. 29, 2016

(51) Int. Cl.
| | |
|---|---|
| *B65D 69/00* | (2006.01) |
| *A47K 13/16* | (2006.01) |
| *A47K 10/20* | (2006.01) |
| *A47K 5/12* | (2006.01) |
| *A01N 59/12* | (2006.01) |
| *A01N 25/10* | (2006.01) |
| *A01N 31/16* | (2006.01) |
| *A01N 47/30* | (2006.01) |
| *A61L 2/23* | (2006.01) |

(52) U.S. Cl.
CPC .............. *A47K 13/16* (2013.01); *A01N 25/10* (2013.01); *A01N 31/16* (2013.01); *A01N 47/30* (2013.01); *A01N 59/12* (2013.01); *A47K 5/12* (2013.01); *A47K 10/20* (2013.01); *A61L 2/23* (2013.01)

(58) Field of Classification Search
CPC .......... A47K 13/16; A47K 10/20; A47K 5/12; A61L 2/23; A01N 59/12; A01N 25/10; A01N 31/16; A01N 47/30
USPC ....... 206/581, 233, 438, 449, 494, 812, 823, 206/570, 210, 205, 223, 229; 4/245.8, 4/245.9
See application file for complete search history.

(56) References Cited

U.S. PATENT DOCUMENTS

| | | | | |
|---|---|---|---|---|
| 3,684,086 | A | * | 8/1972 | Harrison ............ B65D 75/5827 206/449 |
| 4,735,317 | A | * | 4/1988 | Sussman .............. A47K 10/185 206/449 |
| 4,745,640 | A | * | 5/1988 | Nelson .................. A47K 13/14 4/245.6 |
| 4,908,262 | A | * | 3/1990 | Nelson .................. A47K 13/14 4/245.6 |
| 5,242,057 | A | | 9/1993 | Cook |
| 6,196,390 | B1 | * | 3/2001 | Bando ................. A47K 10/421 206/205 |
| D448,479 | S | | 9/2001 | Foy |
| 6,609,616 | B2 | * | 8/2003 | Dilnik ................. A45C 11/008 206/494 |
| 7,104,977 | B2 | | 9/2006 | Price |
| 7,247,360 | B1 | * | 7/2007 | Besner .................. A47K 13/16 4/245.1 |
| 7,774,869 | B2 | | 8/2010 | Massey, Jr. |
| 8,596,458 | B1 | * | 12/2013 | Alcorn ................. A45C 11/008 206/229 |

(Continued)

FOREIGN PATENT DOCUMENTS

WO          9414365 A1       7/1994

*Primary Examiner* — Jacob K Ackun
*Assistant Examiner* — Jenine Pagan

(57) ABSTRACT

The kit of toiletry items is a collection of sanitary devices. The kit of toiletry items is configured for use during sanitary activities associated with the bodily processes of elimination and excretion. The kit of toiletry items comprises a toilet seat cover, a plurality of sanitary wipes, toilet paper, and a container of cleansing solution. The toilet seat cover provides a protective barrier for use with a toilet seat. The toilet seat cover prevents the transfer of pathogens. The toilet paper provides for the primary sanitary services available from the kit. The sanitary wipes and the container of cleansing solution provides a range of secondary sanitary services that are available from the kit.

8 Claims, 1 Drawing Sheet

(56) References Cited

U.S. PATENT DOCUMENTS

2003/0141204 A1 7/2003 Yuskaitis
2006/0283750 A1* 12/2006 Villars ............... B65D 83/0805
 206/494
2008/0308451 A1 12/2008 Riechel
2013/0206640 A1 8/2013 Mann, Jr.

* cited by examiner

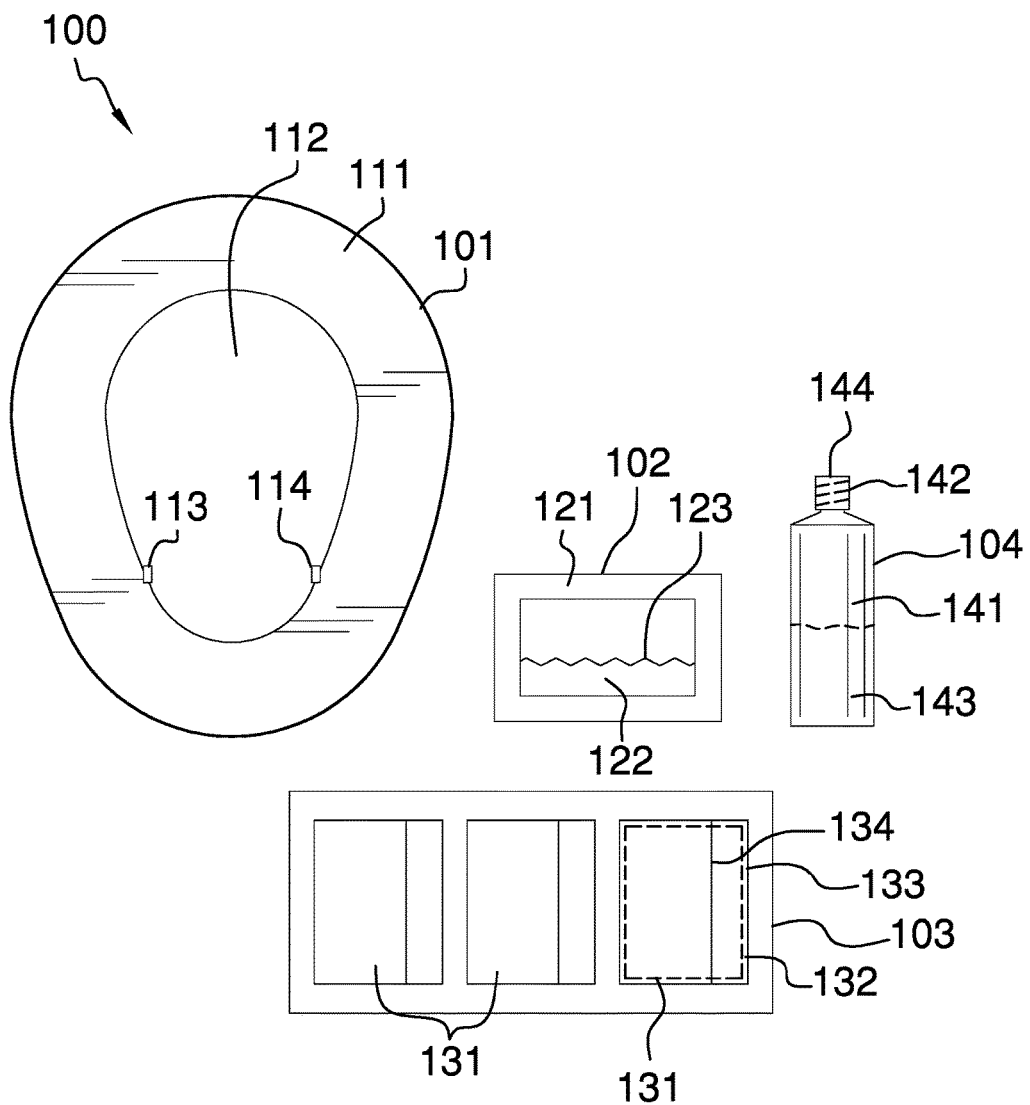

KIT OF TOILETRY ITEMS

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of personal and domestic articles, more specifically, kit of miscellaneous cleaning items configured for use in domestic washing and cleaning.

SUMMARY OF INVENTION

The kit of toiletry items is a collection of sanitary devices. The kit of toiletry items is configured for use during sanitary activities associated with the bodily processes of elimination and excretion. The kit of toiletry items comprises a toilet seat cover, a plurality of sanitary wipes, toilet paper, and a container of cleansing solution. The toilet seat cover provides a protective barrier for use with a toilet seat. The toilet seat cover prevents the transfer of pathogens. The toilet paper provides for the primary sanitary services available from the kit. The sanitary wipes and the container of cleansing solution provides a range of secondary sanitary services available from the kit.

These together with additional objects, features and advantages of the kit of toiletry items will be readily apparent to those of ordinary skill in the art upon reading the following detailed description of the presently preferred, but nonetheless illustrative, embodiments when taken in conjunction with the accompanying drawings.

In this respect, before explaining the current embodiments of the kit of toiletry items in detail, it is to be understood that the kit of toiletry items is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the kit of toiletry items.

It is therefore important that the claims be regarded as including such equivalent construction insofar as they do not depart from the spirit and scope of the kit of toiletry items. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

FIG. 1 is a kit view of an embodiment of the disclosure.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Detailed reference will now be made to one or more potential embodiments of the disclosure, which are illustrated in FIG. 1.

The kit of toiletry items 100 (hereinafter invention) is a collection of sanitary devices. The invention 100 is configured for use during sanitary activities associated with the bodily processes of elimination and excretion. The invention 100 comprises a toilet seat cover 101, a plurality of sanitary wipes 102, toilet paper 103, and a container of cleansing solution 104. The toilet seat cover 101 provides a protective barrier for use with a toilet seat. The toilet seat cover 101 prevents the transfer of pathogens. The toilet paper 103 provides for the primary sanitary services available from the kit. The plurality of sanitary wipes 102 and the container of cleansing solution 104 provides a range of secondary sanitary services that are available from the invention 100.

The toilet seat cover 101 is a disposable sheet of paper that is shaped like a toilet seat. The toilet seat cover 101 is placed on top of the toilet seat before use of the sanitary facilities. In the first potential embodiment of the disclosure, the toilet seat cover 101 is formed from a silicone impregnated paper. The toilet seat cover 101 forms a barrier that inhibits the transfer of pathogens from the toilet seat. The toilet seat cover 101 comprises a coated paper sheet 111, a flap 112, a first tab 113, and a second tab 114.

The coated paper sheet 111 is a silicone-impregnated sheet of paper that is formed in the shape of a toilet seat. The flap 112 is formed from a cut formed within the coated paper sheet 111. The flap 112 is a portion of the coated paper sheet 111 that hangs in a hinged manner away from the coated paper sheet 111. The flap 112 forms an aperture that allows for the free passage of materials discharged through the elimination and excretion processes into an appropriate sanitary facility.

The first tab 113 is a small discontinuity in the cut that forms the flap 112. The second tab 114 is a small discontinuity in the cut that forms the flap 112. The purpose of the first tab 113 is to maintain the attachment of the flap 112 to the coated paper sheet 111 to form a flat sheet until the toilet seat cover 101 is required for use. The second tab 114 is to maintain the attachment of the flap 112 to the coated paper sheet 111 to form a flat sheet until the toilet seat cover 101 is required for use. The first tab 113 and the second tab 114 are broken before the toilet seat cover 101 is used.

The plurality of sanitary wipes 102 is a collection of pre-moistened wipes as well as the associated containment to store the pre-moistened wipes. The plurality of sanitary wipes 102 are used for cleansing after the elimination and excretion processes. The plurality of sanitary wipes 102 comprises a sealed package 121, and a plurality of individual wipes 122. The sealed package 121 further comprises a dispensing aperture 123.

The sealed package 121 is a water impermeable first containment device within which the plurality of individual wipes 122 are contained. The sealed package 121 can be formed as a box or an envelope for the purpose of storing the plurality of individual wipes 122. The dispensing aperture 123 is a hole formed in the sealed package 121 through which each of the plurality of individual wipes 122 is withdrawn.

Each of the plurality of individual wipes 122 is a pre-moistened wipe. Each of the plurality of individual wipes 122 is saturated with an anti-bacterial solution for sanitary purposes. Suitable antibacterial solutions for use in each of the plurality of individual wipes 122 include, but are not limited to, 2-pyrrolidinone with iodine (CAS 25655-41-8) in water, 5-chloro-2-(2,4-dichlorophenoxy)-phenol (CAS 3380-34-5) in water, or N-(4-chlorophenyl)-N'-(3,4-dichlorophenyl)-urea (CAS 101-20-2) in water. Each of the plurality of individual wipes 122 is used for cleansing after the elimination and excretion processes.

The plurality of individual wipes 122 are folded in a well-known and interlocking manner that allows for a second pre-moistened wipe selected from the plurality of individual wipes 122 to "pop up" after a first pre-moistened wipe selected from the plurality of individual wipes 122 is removed from the sealed package 121.

The toilet paper 103 comprises a plurality of packages 131, a plurality of toilet paper sheets 132, envelope 133, and a dispensing slit 134. The toilet paper 103 is a readily and commercially collection of individual toilet paper 103 sheets. The toilet paper 103 is used for cleansing after the elimination and excretion processes.

Each of the plurality of packages 131 is a second containment device within which each of the plurality of toilet paper sheets 132 is stored. It is preferred that each of the plurality of packages 131 is formed as an envelope 133.

The plurality of toilet paper sheets 132 is a collection of flat sheets of toilet paper that are contained within a package selected from the plurality of packages 131. Each of the plurality of toilet paper sheets 132 are folded in a well-known and interlocking manner that allows for a second toilet paper sheet selected from the plurality of toilet paper sheets 132 to "pop up" after a first toilet paper sheet selected from the plurality of toilet paper sheets 132 is removed.

The envelope 133 is a flat containment device formed from a single-folded sheeting.

The dispensing slit 134 is an aperture formed within the envelope 133 through which each of the plurality of toilet paper sheets 132 is removed from the envelope 133.

The container of cleansing solution 104 comprises a liquid container 141, a lid 142, and a liquid soap 143. The container of cleansing solution 104 is a bottle that contains a cleansing solution. In the first potential embodiment of the disclosure, the cleansing solution is a liquid soap 143. The liquid soap 143 is used for cleansing after the elimination and excretion processes. The liquid container 141 is a bottle that contains the liquid soap 143. The liquid container 141 is further defined with a neck. The lid 142 is a covering that is used to contain the liquid soap 143 within the liquid container 141. The lid 142 attaches to the neck using a threaded connection 144. The use of threaded connections 144 to form fluid impermeable seals is well known and documented in the mechanical and plumbing arts. The liquid soap 143 is a readily and commercially available soap that is delivered in a liquid form.

The following definitions were used in this disclosure:

2-pyrrolidinone with iodine: As used in this disclosure, 2-pyrrolidinone with iodine (CAS 25655-41-8) is an antiseptic chemical substance commonly referred to a povidone-iodine.

5-chloro-2-(2,4-dichlorophenoxy)-phenol: As used in this disclosure, 5-chloro-2-(2,4-dichlorophenoxy)-phenol (CAS 3380-34-5) is an antifungal and antibiotic agent that is commonly used in consumer products. 5-chloro-2-(2,4-dichlorophenoxy)-phenol is commonly referred to as triclosan.

Bottle: As used in this disclosure, a bottle is a container used for the storage of fluids. Access to the interior of a bottle is gained through the neck of the bottle. The neck is an elongated tube that forms an aperture through which fluids can be introduced and removed from the bottle.

Carboxylic Acid: As used in this disclosure, a carboxylic acid is an organic molecule that further comprises the carboxyl functional group.

Carboxyl Functional Group: As used in this disclosure, the carboxyl functional group is a functional group with the chemical formula —COOH.

Envelope: As used in this disclosure, an envelope is a readily and commercially available flat folded container that is formed from a paper or plastic sheeting. Envelopes will generally have a method of sealing contents contained within the envelope.

Exterior: As used in this disclosure, the exterior is use as a relational term that implies that an object is not contained within the boundary of a structure or a space.

Fatty Acid: As used in this disclosure, a fatty acid refers to a carboxylic acid with a continuous carbon chain of greater than 3 carbon atoms beyond the carboxyl functional group.

Flap: As used in this disclosure, a flap is a piece of material that is hinged or otherwise attached to a surface using one side such that the piece of material hangs in such a way as to cover a hole in the surface.

Functional Group: As used in this disclosure, a functional group is specific chemical structure that 1) defines the structure of a chemical family; and, 2) determines the properties of the chemical family. Common functional groups include, but are not limited to, aldehydes, alkanes, alkenes, alkynes, alcohols, amides, amines, carboxylic acids, esters, ethers, haloalkanes, haloalkanes, haloalkynes, and ketones. As a practical matter, the intention of this definition is to use the term functional group in the same manner as the term is commonly used in organic chemistry.

Interior: As used in this disclosure, the interior is use as a relational term that implies that an object is contained within the boundary of a structure or a space.

N-(4-chlorophenyl)-N'-(3,4-dichlorophenyl)-urea: As used in this disclosure, N-(4-chlorophenyl)-N'-(3,4-dichlorophenyl)-urea (CAS 101-20-2) is an antibacterial agent commonly found in soaps. N-(4-chlorophenyl)-N'-(3,4-dichlorophenyl)-urea is commonly called triclocarban.

Pre-Moistened Wipe: As used in this disclosure, a pre-moistened wipe is a paper or textile is that previously moistened and that is used for cleaning purposes. By previously moistened is meant that the paper or textile is moistened before the pre-moistened wipe is packaged for storage. These previously moistened papers or textiles will remain moist until subsequent accessed. The previously moistened paper or textile can be individually wrapped for storage or can be stored in bulk. Pre-moistened wipe are commonly referred to a baby wipes or wet wipes.

Salt: As used in this disclosure, a salt means an ionic compound that further comprises at least one atom of a metallic element or compound and one atom of a non-metallic element or compound. When dissolved in water, the ionic compound releases the metallic element and the non-metallic element into the water as ions. In this disclosure, a metallic element is assumed to include the alkali metals and the alkali earth metals. Alternatively, and equivalently, a metallic element may be assumed to be any element on the periodic table that is to the left of the metalloids.

Sheeting: As used in this disclosure, sheeting is a material, such as a textile, a plastic, or a metal foil, in the form of a thin flexible layer or layers.

Silicone: As used in this disclosure, silicone is a substance formed from silicon (Si) and oxygen (O) that forms the backbone of polymer type chains similar to polymers that are formed by carbon.

Soap: As used in this disclosure, a soap is a cleansing agent generally formed from a mixture of one or more salts and one or more fatty acids.

Threaded Connection: As used in this disclosure, a threaded connection is a type of fastener that is used to join a first tube shaped and a second tube shaped object together. The first tube shaped object is fitted with fitted with a first fitting selected from an interior screw thread or an exterior screw thread. The second tube shaped object is fitted with the remaining screw thread. The tube shaped object fitted with the exterior screw thread is placed into the remaining tube shaped object such that: 1) the interior screw thread and the exterior screw thread interconnect; and, 2) when the tube shaped object fitted with the exterior screw thread is rotated the rotational motion is converted into linear motion that moves the tube shaped object fitted with the exterior screw thread either into or out of the remaining tube shaped object. The direction of linear motion is determined by the direction of rotation.

With respect to the above description, it is to be realized that the optimum dimensional relationship for the various components of the invention described above and in FIGS. 1 through 1 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

The inventor claims:

1. A kit of miscellaneous cleaning items comprising:
   a plurality of sanitary wipes, toilet paper, toilet seat cover and a container of cleansing solution;
   wherein the toilet seat cover provides a protective barrier for use with a toilet seat;
   wherein the toilet seat cover prevents the transfer of pathogens;
   wherein the toilet paper provides for the primary sanitary services available from the kit;
   wherein the plurality of sanitary wipes and the container of cleansing solution provide secondary sanitary services;
   wherein the kit of miscellaneous cleaning items is a collection of sanitary devices;
   wherein the kit of miscellaneous cleaning items is configured for use during sanitary activities associated with the bodily processes of elimination and excretion;
   wherein the toilet seat cover is a disposable sheet of paper that is shaped like a toilet seat;
   wherein the toilet seat cover comprises a sheet of silicone impregnated paper;
   wherein a flap is formed from a cut formed within the sheet of silicone impregnated paper;
   wherein the flap is a portion of the sheet of silicone impregnated paper that hangs in a hinged manner away from the coated paper sheet;
   wherein the flap forms an aperture that allows for the free passage of materials discharged through the elimination and excretion processes into an appropriate sanitary facility;
   wherein the toilet seat cover further comprises a first tab, and a second tab;
   wherein the first tab is a small discontinuity in the cut that forms the flap;
   wherein the second tab is a small discontinuity in the cut that forms the flap;
   wherein the first tab maintains the attachment of the flap to the sheet of silicone impregnated paper to form a flat sheet;
   wherein the second tab is to maintain the attachment of the flap to the sheet of silicone impregnated paper to form a flat sheet;
   wherein the first tab and the second tab are broken before the toilet seat cover is used;
   wherein the plurality of sanitary wipes comprises a sealed package, and a plurality of individual wipes;
   wherein the plurality of individual wipes are stored within the sealed package;
   wherein the sealed package further comprises a dispensing aperture;
   wherein the dispensing aperture is a hole formed in the sealed package through which each of the plurality of individual wipes is withdrawn;
   wherein the sealed package is a water impermeable first containment device;
   wherein the sealed package is formed as an object selected from the group consisting of a box or a first envelope;
   wherein each of the plurality of individual wipes is a pre-moistened wipe;
   wherein each of the plurality of individual wipes is saturated with an anti-bacterial solution;
   wherein each of the plurality of individual wipes are folded in a interlocking manner that allows for a second pre-moistened wipe selected from the plurality of individual wipes to "pop up" after a first pre-moistened wipe selected from the plurality of individual wipes is removed from the sealed package;
   wherein the antibacterial solution comprises 2-A pyrrolidinone with iodine in water;
   wherein the toilet paper comprises a plurality of packages, a plurality of toilet paper sheets, envelope, and a dispensing slit;

wherein the toilet paper is a collection of individual toilet paper sheets;

wherein each of the plurality of packages is a second containment device;

wherein the plurality of toilet paper sheets is a collection of flat sheets of toilet paper that are contained within a package selected from the plurality of packages;

wherein each of the plurality of toilet paper sheets are folded in a manner that allows for a second toilet paper sheet selected from the plurality of toilet paper sheets to "pop up" after a first toilet paper sheet selected from the plurality of toilet paper sheets is removed;

wherein the dispensing slit is an aperture formed within the envelope through which each of the plurality of toilet paper sheets is removed from the envelope;

wherein the envelope is a flat containment device formed from a single folded sheeting;

wherein each of the plurality of packages is formed as an envelope.

2. The kit of miscellaneous cleaning items according to claim 1 wherein the container of cleansing solution comprises a liquid container, a lid, and a liquid soap;

wherein the liquid container is a bottle that contains the liquid soap;

wherein the liquid container is further defined with a neck;

wherein the lid is a covering that is used to contain the liquid soap within the liquid container;

wherein the lid attaches to the neck using a threaded connection.

3. The kit of miscellaneous cleaning items according to claim 1 wherein the antibacterial solution comprises 5-chloro-2-(2,4-dichlorophenoxy)-phenol (CAS 3380-34-5) in water.

4. The kit of miscellaneous cleaning items according to claim 3 wherein the toilet paper comprises a plurality of packages, a plurality of toilet paper sheets, envelope, and a dispensing slit;

wherein the toilet paper is a collection of individual toilet paper sheets;

wherein each of the plurality of packages is a second containment device;

wherein the plurality of toilet paper sheets is a collection of flat sheets of toilet paper that are contained within a package selected from the plurality of packages;

wherein each of the plurality of toilet paper sheets are folded in a manner that allows for a second toilet paper sheet selected from the plurality of toilet paper sheets to "pop up" after a first toilet paper sheet selected from the plurality of toilet paper sheets is removed;

wherein the dispensing slit is an aperture formed within the envelope through which each of the plurality of toilet paper sheets is removed from the envelope;

wherein the envelope is a flat containment device formed from a single folded sheeting;

wherein each of the plurality of packages is formed as an envelope.

5. The kit of miscellaneous cleaning items according to claim 4 wherein the container of cleansing solution comprises a liquid container, a lid, and a liquid soap;

wherein the liquid container is a bottle that contains the liquid soap;

wherein the liquid container is further defined with a neck;

wherein the lid is a covering that is used to contain the liquid soap within the liquid container;

wherein the lid attaches to the neck using a threaded connection.

6. The kit of miscellaneous cleaning items according to claim 1 wherein the antibacterial solution comprises N-(4-chlorophenyl)-N'-(3,4-dichlorophenyl)-urea (CAS 101-20-2) in water.

7. The kit of miscellaneous cleaning items according to claim 6 wherein the toilet paper comprises a plurality of packages, a plurality of toilet paper sheets, envelope, and a dispensing slit;

wherein the toilet paper is a collection of individual toilet paper sheets;

wherein each of the plurality of packages is a second containment device;

wherein the plurality of toilet paper sheets is a collection of flat sheets of toilet paper that are contained within a package selected from the plurality of packages;

wherein each of the plurality of toilet paper sheets are folded in a manner that allows for a second toilet paper sheet selected from the plurality of toilet paper sheets to "pop up" after a first toilet paper sheet selected from the plurality of toilet paper sheets is removed;

wherein the dispensing slit is an aperture formed within the envelope through which each of the plurality of toilet paper sheets is removed from the envelope;

wherein the envelope is a flat containment device formed from a single folded sheeting;

wherein each of the plurality of packages is formed as an envelope.

8. The kit of miscellaneous cleaning items according to claim 7 wherein the container of cleansing solution comprises a liquid container, a lid, and a liquid soap;

wherein the liquid container is a bottle that contains the liquid soap;

wherein the liquid container is further defined with a neck;

wherein the lid is a covering that is used to contain the liquid soap within the liquid container;

wherein the lid attaches to the neck using a threaded connection.

* * * * *